United States Patent
Shimizu et al.

(10) Patent No.: US 11,873,275 B2
(45) Date of Patent: Jan. 16, 2024

(54) PERFLUOROPOLYETHER COMPOUND, LUBRICANT, AND MAGNETIC DISK

(71) Applicant: MORESCO CORPORATION, Kobe (JP)

(72) Inventors: Tsuyoshi Shimizu, Hyogo (JP); Akinori Kimura, Hyogo (JP)

(73) Assignee: Moresco Corporation, Kobe (JP)

( * ) Notice: Subject to any disclaimer, the term of this patent is extended or adjusted under 35 U.S.C. 154(b) by 157 days.

(21) Appl. No.: 17/616,867

(22) PCT Filed: May 18, 2020

(86) PCT No.: PCT/JP2020/019683
§ 371 (c)(1),
(2) Date: Dec. 6, 2021

(87) PCT Pub. No.: WO2020/250627
PCT Pub. Date: Dec. 17, 2020

(65) Prior Publication Data
US 2022/0315514 A1     Oct. 6, 2022

(30) Foreign Application Priority Data
Jun. 10, 2019   (JP) .................... 2019-107981

(51) Int. Cl.
*C07C 43/29* (2006.01)
*C10M 107/38* (2006.01)
(Continued)

(52) U.S. Cl.
CPC ............ *C07C 43/29* (2013.01); *C07C 43/225* (2013.01); *C10M 107/38* (2013.01); *G11B 5/725* (2013.01)

(58) Field of Classification Search
CPC .... C07C 43/29; C07C 43/225; C10M 107/38; C10M 2213/043; C10M 2213/0606;
(Continued)

(56) References Cited

U.S. PATENT DOCUMENTS

| 5,073,466 A | 12/1991 | Ishikawa et al. |
| 11,651,789 B2 * | 5/2023 | Kimura ................ G11B 5/7257 428/848 |

(Continued)

FOREIGN PATENT DOCUMENTS

| JP | H0262551 A | 3/1990 |
| JP | H09035252 A | 2/1997 |

(Continued)

OTHER PUBLICATIONS

International Search Report from corresponding PCT Application No. PCT/JP2020/019683 dated Jul. 14, 2020.
(Continued)

*Primary Examiner* — Ellen M McAvoy
(74) *Attorney, Agent, or Firm* — Harness Dickey & Pierce P.L.C.

(57) ABSTRACT

Provided is a compound which allows realization of a lubricant having high adsorbability and a high covering property with respect to a magnetic disk, particularly a carbon protective film. A perfluoropolyether compound in accordance with an aspect of the present invention has a naphthyl group or a phenoxyphenyl group at any one of terminals thereof.

3 Claims, 1 Drawing Sheet

(51) Int. Cl.
*C07C 43/225* (2006.01)
*G11B 5/725* (2006.01)

(58) Field of Classification Search
CPC .. G11B 5/725; G11B 5/7257; C10N 2040/18; C10N 2050/023
See application file for complete search history.

(56) References Cited

U.S. PATENT DOCUMENTS

| | | |
|---|---|---|
| 2010/0239887 A1 | 9/2010 | Kobayashi |
| 2010/0261039 A1 | 10/2010 | Itoh et al. |
| 2013/0209837 A1 | 8/2013 | Sagata et al. |
| 2014/0147699 A1 | 5/2014 | Kobayashi |
| 2015/0371672 A1 | 12/2015 | Sagata |
| 2018/0009773 A1* | 1/2018 | Uetake .................... C07C 43/23 |
| 2019/0084911 A1 | 3/2019 | Yagyu et al. |
| 2021/0062102 A1* | 3/2021 | Kato ..................... C10M 105/54 |
| 2021/0155751 A1* | 5/2021 | Kato ..................... C07C 233/25 |
| 2021/0188766 A1* | 6/2021 | Nanko .................. C07C 255/17 |
| 2022/0093127 A1* | 3/2022 | Kimura ................ C08G 65/329 |

FOREIGN PATENT DOCUMENTS

| | | |
|---|---|---|
| JP | 2009266360 A | 11/2009 |
| JP | 2013163667 A | 8/2013 |
| WO | 2009066784 A1 | 5/2009 |
| WO | 2015087615 A1 | 6/2015 |
| WO | 2017154403 A1 | 9/2017 |

OTHER PUBLICATIONS

International Preliminary Report on Patentability from corresponding PCT Application No. PCT/JP2020/019683 dated Jul. 14, 2020.

* cited by examiner

PERFLUOROPOLYETHER COMPOUND, LUBRICANT, AND MAGNETIC DISK

TECHNICAL FIELD

The present invention relates to a perfluoropolyether compound, a lubricant, and a magnetic disk.

BACKGROUND ART

Many of the existing magnetic disks are constituted by: a recording layer disposed on a substrate; a protective layer disposed on the recording layer in order to protect information recorded on the recording layer; and a lubricant layer disposed on the protective layer.

In order to increase the recording density of a magnetic disk, it is required to cause a lubricant layer, which is applied to a disk surface, to be a thinner film.

As conventional techniques concerning surface lubricants for magnetic disks, the techniques disclosed in Patent Literatures 1 to 4 are, for example, known. Patent Literatures 1 to 4 disclose various perfluoropolyether compounds.

CITATION LIST

Patent Literature

[Patent Literature 1]
International Publication No. WO 2009/066784
[Patent Literature 2]
Japanese Patent Application Publication Tokukai No. 2013-163667
[Patent Literature 3]
Japanese Patent Application Publication Tokukai No. 2009-266360
[Patent Literature 4]
International Publication No. WO 2015/087615

SUMMARY OF INVENTION

Technical Problem

In a case where a lubricant layer is caused to be a thin film, a part of a carbon protective film (the foregoing protective layer) on a disk surface having high surface energy is exposed, and foreign matters such as siloxane can adhere to such an exposed part. Such adhesion of foreign matters is a factor in preventing flotation of a head from being lowered. Therefore, demanded is a lubricant which has a favorable covering property even when caused to be a thin film and which causes siloxane not to easily adhere to a carbon protective film.

However, the conventional techniques as described above still have room for improvement, from the viewpoint of preventing adsorption of siloxane on a carbon protective film (i.e., carbon material surface) by sufficiently covering the carbon protective film.

An object of an aspect of the present invention is to provide a compound which allows realization of a lubricant having high adsorbability and a high covering property with respect to a magnetic disk, particularly a carbon protective film.

Solution to Problem

As a result of conducting diligent studies in order to attain the above object, the inventors of the present invention found that a compound having a polycyclic aromatic substituent such as a naphthyl group or a phenoxyphenyl group has excellent adsorbability and exhibits favorable siloxane resistance, thereby completing the present invention. That is, the present invention includes the following aspects.

<1> A perfluoropolyether compound represented by the following formula (1):

wherein: $R^1$ is a naphthyl group represented by $C_{10}H_7$— or a phenoxyphenyl group represented by $C_6H_5$—$OC_6H_4$—; $R^2$ is —$(CF_2)_x(CF(CF_3))_yO(CF_2O)_z(CF_2CF_2O)_l(CF_2CF_2CF_2O)_m(CF_2CF_2CF_2CF_2O)_n(CF(CF_3)CF_2O)_o(CF(CF_3))_y(CF_2)_x$—, wherein x is a real number of 0 to 3, y is a real number of 0 to 1, z, l, m, n, and o are each independently a real number of 0 to 15, and any one of x and y is a real number of 1 or more and at least any one of z, l, m, n, and o is a real number of 1 or more; and $R^3$ is a hydrocarbon group having a naphthyl group represented by —$CH_2OCH_2CH(OH)CH_2O$—$C_{10}H_7$, a hydrocarbon group having a phenoxyphenyl group represented by —$CH_2OCH_2CH(OH)CH_2O$—$C_6H_4$—$OC_6H_5$, a hydrocarbon group having a methoxyphenyl group represented by —$CH_2OCH_2CH(OH)CH_2O$—$C_6H_4$—OMe, or —$CH_2O(CH_2CH(OH)CH_2O)_tH$ or —$(CF_2)_uCF_3$, wherein t is a real number of 0 to 5 and u is a real number of 0 to 3.

<2> A lubricant including a perfluoropolyether compound described in <1>.

<3> A magnetic disk including: a recording layer; a protective layer disposed on the recording layer; and a lubricant layer disposed on the protective layer, the lubricant layer containing a lubricant described in <2>.

Advantageous Effects of Invention

According to an aspect of the present invention, it is possible to provide a compound which allows realization of a lubricant having high adsorbability and a high covering property with respect to a magnetic disk, particularly a carbon protective film.

DESCRIPTION OF EMBODIMENTS

The following description will discuss embodiments of the present invention in detail. Note, however, that the present invention is not limited to the embodiments, but can be altered within this disclosure. The present invention also encompasses, in its technical scope, any embodiment derived by combining technical means disclosed in differing embodiments. Note that the expression "A to B", representing a numerical range, herein means "not less than A but not more than B" unless otherwise specified in this specification.

[1. Perfluoropolyether Compound]

A perfluoropolyether compound in accordance with an embodiment of the present invention has a structure represented by the following formula (1):

wherein: $R^1$ is a naphthyl group represented by $C_{10}H_7$— or a phenoxyphenyl group represented by $C_6H_5$—$OC_6H_4$—;

$R^2$ is —$(CF_2)_x(CF(CF_3))_yO(CF_2O)_z(CF_2CF_2O)_l(CF_2CF_2CF_2O)_m(CF_2CF_2CF_2CF_2O)_n(CF(CF_3)CF_2O)_o(CF(CF_3))_y(CF_2)_x$—, wherein x is a real number of 0 to 3, y is a real number of 0 to 1, z, 1, m, n, and o are each independently a real number of 0 to 15, and any one of x and y is a real number of 1 or more and at least any one of z, l, m, n, and o is a real number of 1 or more; and $R^3$ is a hydrocarbon group having a naphthyl group represented by —$CH_2OCH_2CH(OH)CH_2O$—$C_{10}H_7$, a hydrocarbon group having a phenoxyphenyl group represented by —$CH_2OCH_2CH(OH)CH_2O$—$C_6H_4$—$OC_6H_5$, a hydrocarbon group having a methoxyphenyl group represented by —$CH_2OCH_2CH(OH)CH_2O$—$C_6H_4$—OMe, or —$CH_2O(CH_2CH(OH)CH_2O)_tH$ or —$(CF_2)_uCF_3$, wherein t is a real number of 0 to 5 and u is a real number of 0 to 3.

In order to develop a lubricant which is less likely to attract siloxane, the inventors of the present invention performed simulation of model compounds having various substituents and made small amounts of prototypes of the model compounds. As a result, the inventors of the present invention found that a compound having a polycyclic aromatic substituent such as a naphthyl group or a phenoxyphenyl group has excellent adsorbability and exhibits favorable siloxane resistance. The inventors of the present invention then (i) synthesized lubricants into which these substituents were introduced, (ii) conducted various studies, and (iii) optimized the lubricants. Consequently, the inventors of the present invention found conditions under which the lubricants had excellent adsorbability and favorable siloxane resistance. The lubricants each exhibit favorable siloxane resistance because the lubricants each form a film that efficiently covers a magnetic disk.

In this specification, whether a lubricant has "excellent adsorbability" can be evaluated by carrying out adsorbability evaluation described in Examples. In this specification, whether a lubricant has an "excellent covering property" can be evaluated by carrying out siloxane resistance evaluation described in Examples. The siloxane resistance evaluation evaluates how easily siloxane, which is a typical impurity that can contaminate a magnetic disk during a process of manufacturing the magnetic disk, adheres to a carbon protective layer.

The perfluoropolyether compound in accordance with an embodiment of the present invention is not limited to any particular one, provided that the perfluoropolyether compound is represented by the foregoing formula (1). The perfluoropolyether compound contains any combination of $R^1$ to $R^3$ described above.

Examples of $R^2$ include a Demnum skeleton: —$CF_2CF_2O$—$(CF_2CF_2O)_mCF_2CF_2$—, a Fomblin skeleton: —$CF_2O$—$(CF_2O)_z(CF_2CF_2O)_lCF_2$—, a C2 skeleton: —$CF_2O$—$(CF_2CF_2O)_lCF_2$—, a C4 skeleton: —$CF_2CF_2CF_2O$—$(CF_2CF_2CF_2CF_2O)_nCF_2CF_2CF_2$—, and a Krytox skeleton: $CF(CF_3)O$—$(CF(CF_3)CF_2O)_oCF(CF_3)$—. In the above skeletons, z, l, m, n, and o are each independently a real number of 1 to 15. Note that in the Fomblin skeleton, $CF_2O$ and $CF_2CF_2O$ can be randomly repeated.

Examples of $R^3$ includes a hydrocarbon group having a naphthyl group represented by —$CH_2OCH_2CH(OH)CH_2O$—$C_{10}H_7$, a hydrocarbon group having a phenoxyphenyl group represented by —$CH_2OCH_2CH(OH)CH_2O$—$C_6H_4$—$OC_6H_5$, a hydrocarbon group having a methoxyphenyl group represented by —$CH_2OCH_2CH(OH)CH_2O$—$C_6H_4$—OMe, a hydrocarbon group having a dihydroxypropoxy group represented by —$CH_2OCH_2CH(OH)CH_2OH$, and a trifluoromethyl group represented by —$CF_3$. $R^3$ is preferably a hydrocarbon group having a naphthyl group, a hydrocarbon group having a phenoxyphenyl group, and a hydrocarbon group having a dihydroxypropoxy group.

[2. Method of Producing Perfluoropolyether Compound]

A method of producing the perfluoropolyether compound in accordance with an embodiment of the present invention is not limited to any particular one. The perfluoropolyether compound can be obtained, for example, by causing a linear fluoropolyether (a) having a hydroxy group(s) at a terminal(s) thereof and a naphthalene derivative (A) having an epoxy group or a phenoxybenzene derivative (B) having an epoxy group to react with each other.

For example, in a case where the perfluoropolyether compound which has the Demnum skeleton is obtained, the linear fluoropolyether (a) having a hydroxy group(s) at a terminal(s) thereof is, for example, a compound represented by $HOCH_2$—$CF_2CF_2O$—$(CF_2CF_2CF_2O)_vCF_2CF_2$—$CH_2OH$. The number average molecular weight of this linear fluoropolyether is preferably 500 to 4000, and more preferably 800 to 2000. Note, here, that the number average molecular weight is a value measured by $^{19}$F-NMR with use of JNM-ECX400 available from JEOL Ltd. In the NMR measurement, a sample (linear fluoropolyether) is used as it is without being diluted with a solvent. A known peak that indicates a part of a skeleton structure of fluoropolyether is used as a reference for a chemical shift. Note that v is a real number of 1 to 15, and preferably a real number of 3 to 12. In a case where v is a real number of 3 to 12, the molecular chain becomes flatter. Thus, it is preferable that v be a real number of 3 to 12.

Note that in a case where the perfluoropolyether compound which has a skeleton other than the Demnum skeleton is obtained, a linear fluoropolyether having a desired skeleton and having a hydroxy group(s) at a terminal(s) thereof can be similarly used.

The linear fluoropolyether (a) may have hydroxy groups at both terminals thereof or may alternatively have a hydroxy group at one terminal thereof and have, at the other terminal thereof, a trifluoromethyl group or the like listed as the examples of $R^3$ described above.

The linear fluoropolyether (a) is a compound having a molecular weight distribution, and has a molecular weight distribution (PD), represented by weight average molecular weight/number average molecular weight, of preferably 1.0 to 1.5, more preferably 1.0 to 1.3, and even more preferably 1.0 to 1.1. Note that the molecular weight distribution is a property value obtained with use of HPLC-8220GPC available from Tosoh Corporation, a column (PLgel Mixed E) available from Polymer Laboratories, an HCFC-based substitute for CFCs as an eluent, and a non-functional perfluoropolyether as a reference substance.

A method of synthesizing the naphthalene derivative (A) having an epoxy group or the phenoxybenzene derivative (B) having an epoxy group is not limited to any particular one. For example, a naphthalene compound having a hydroxy group or a phenoxybenzene compound having a hydroxy group and a halogenated alkane having an epoxy group are heated and stirred in the presence of an alkaline compound such as sodium t-butoxide or potassium t-butoxide. A reaction temperature is preferably 10° C. to 90° C., and more preferably 60° C. to 80° C. A reaction time is preferably 2 hours to 20 hours, and more preferably 10 hours to 18 hours. The halogenated alkane having an epoxy group is used in an amount of preferably 20 equivalents to 30 equivalents with respect to the naphthalene compound having a hydroxy group or the phenoxybenzene compound having a hydroxy group. The alkaline compound is used in an amount of preferably 1.0 equivalent to 2.0 equivalents with respect to the naphthalene compound having a hydroxy group or the phenoxybenzene compound having a hydroxy group. Thereafter, a resulting reaction product is refined, for example, by silica gel column chromatography to obtain (A) or (B).

Examples of the naphthalene compound having a hydroxy group include $C_{10}H_7$—OH, and examples of the phenoxybenzene compound having a hydroxy group include $C_6H_5$—$OC_6H_4$—OH.

Examples of the halogenated alkane having an epoxy group include a compound represented by AY (A represents alkyl having 1 to 5 carbon atoms, and Y represents a halogen such as chlorine, bromine, or iodine). Specifically, the halogenated alkane having an epoxy group is epichlorohydrin, epibromohydrin, or the like.

The perfluoropolyether compound in accordance with an embodiment of the present invention can be synthesized, specifically, by the following method. First, the linear fluoropolyether (a) having a hydroxy group(s) at a terminal(s) thereof and (A) or (B) are caused to react with each other in the presence of a catalyst. A reaction temperature is 20° C. to 90° C., and preferably 60° C. to 80° C. A reaction time is 5 hours to 20 hours, and preferably 10 hours to 18 hours. (A) or (B) is preferably used in an amount of 0.3 equivalents to 3.0 equivalents with respect to (a), and the catalyst is preferably used in an amount of 0.05 equivalents to 0.5 equivalents with respect to (a). As the catalyst, an alkaline compound such as sodium t-butoxide or potassium t-butoxide can be used. The reaction may be carried out in a solvent. Examples of the solvent include t-butyl alcohol, toluene, and xylene. Thereafter, a resulting reaction product is refined, for example, by water washing or silica gel column chromatography. As a result, the perfluoropolyether compound represented by the foregoing formula (1) is obtained.

[3. Lubricant]

A lubricant in accordance with an embodiment of the present invention contains the perfluoropolyether compound in accordance with an embodiment of the present invention. The perfluoropolyether compound can be also used alone as the lubricant. Alternatively, the perfluoropolyether compound and any other component which are mixed at a certain ratio may be used as the lubricant, provided that the performance of the lubricant is not impaired.

Examples of the any other component include: known lubricants for magnetic disks, such as Fomblin (registered trademark) Zdol (available from Solvay Solexis), Ztetraol (available from Solvay Solexis), Demnum (registered trademark) (available from Daikin Industries, Ltd.), and Krytox (registered trademark) (available from DuPont); PHOSFAROL A20H (MORESCO PHOSFAROL A20H) (available from MORESCO Corporation); and MORESCO PHOSFAROL D-40H (available from MORESCO Corporation).

The lubricant can be used as a lubricant for recording media, in order to improve the sliding properties of magnetic disks. The lubricant can also be used as a lubricant for recording media (e.g., magnetic tapes) other than magnetic disks, in recording devices that involve sliding between the recording media and heads. The lubricant can also be used as a lubricant for other apparatuses which have parts that involve sliding, not confined to the recording devices.

[4. Magnetic Disk]

Figure 1:
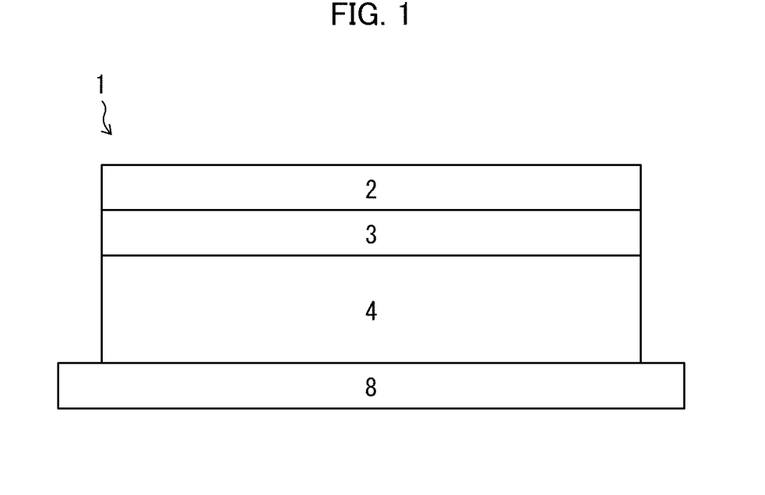
FIG. 1 is a cross-sectional view illustrating a configuration of a magnetic disk in accordance with an embodiment of the present invention.

A magnetic disk 1 in accordance with an embodiment of the present invention includes, as illustrated in FIG. 1, a recording layer 4, a protective film layer (protective layer) 3, and a lubricant layer 2, which are disposed on a non-magnetic substrate 8. The lubricant layer 2 contains the foregoing lubricant.

Figure 2:
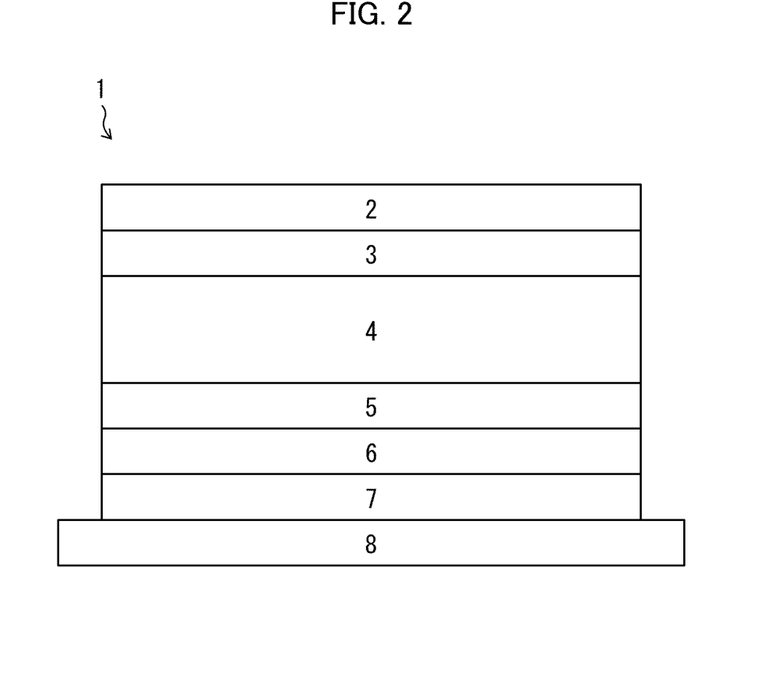
FIG. 2 is a cross-sectional view illustrating a configuration of a magnetic disk in accordance with an embodiment of the present invention.

In another embodiment, the magnetic disk can include, like a magnetic disk 1 illustrated in FIG. 2, a lower layer 5 that underlies the recording layer 4, one or more soft magnetic lower layers 6 that underlie the lower layer 5, and an adhesive layer 7 that underlies the one or more soft magnetic lower layers 6. In an embodiment, all these layers can be formed on the non-magnetic substrate 8.

Each of the layers of the magnetic disk 1 other than the lubricant layer 2 can contain a material that is known in this technical field to be suitable for a corresponding one of layers of a magnetic disk. Examples of the material of the recording layer 4 include: an alloy of an element (e.g., iron, cobalt, and nickel) from which a ferromagnetic material can be formed and chromium, platinum, tantalum or the like; and an oxide of the alloy. Examples of the material of the protective layer 3 include carbon, $Si_3N_4$, SiC, and $SiO_2$. Examples of the material of the non-magnetic substrate 8 include an aluminum alloy, glass, and polycarbonate.

[5. Method of Producing Magnetic Disk]

A method of producing the magnetic disk in accordance with an aspect of the present invention includes a step of forming a lubricant layer by placing the lubricant in accordance with an embodiment of the present invention on an exposed surface of a protective layer of a stack of a recording layer and the protective layer.

There is no particular limitation on a method of forming the lubricant layer by placing the lubricant on the exposed surface of the protective layer of the stack of the recording layer and the protective layer. It is preferable that the lubricant be placed on the exposed surface of the protective layer by the following method: the lubricant is diluted with a solvent and then placed on the exposed surface. Examples of the solvent include: PF-5060, PF-5080, HFE-7100, and HFE-7200 available from 3M; and Vertrel-XF (registered trademark) available from DuPont. The lubricant diluted with the solvent has a concentration of preferably 0.001 wt % to 1 wt %, more preferably 0.005 wt % to 0.5 wt %, and even more preferably 0.01 wt % to 0.1 wt %. In a case where the concentration of the lubricant diluted with the solvent is 0.01 wt % to 0.1 wt %, the viscosity of the lubricant is low enough to easily control the thickness of the lubricant layer.

The lubricant layer may be formed by the following method: the recording layer and the protective layer are formed in this order; the lubricant is placed on the exposed surface of the protective layer; and then ultraviolet irradiation or heat treatment is carried out.

Carrying out ultraviolet irradiation or heat irradiation makes it possible to form stronger bonds between the lubricant layer and the exposed surface of the protective layer and, in turn, prevent the lubricant from evaporating from heat. In a case where ultraviolet irradiation is carried out, it is preferable to use an ultraviolet ray having a wavelength of 185 nm or 254 nm as the dominant wavelength, in order to activate the exposed surface without affecting deep areas of the lubricant layer and the protective layer. The temperature of the heat treatment is preferably 60° C. to 170° C., more preferably 80° C. to 170° C., and even more preferably 80° C. to 150° C.

EXAMPLES

The present invention will be described below in more detail with reference to Examples. Note, however, that the present invention is not limited to such Examples. Note that adsorbability evaluation and siloxane resistance evaluation in Examples below were carried out by the following methods.

[Adsorbability Evaluation]

A lubricant (0.15 g) (described later) was dissolved in Vertrel-XF (150 g) (registered trademark) available from DuPont, and a resulting solution was stirred for 1 hour. A lubricant solution was thus prepared. Subsequently, Graphite powder <20 μm (1.0 g) available from Aldrich was added to the resulting lubricant solution, and then the lubricant solution was stirred for another 1 hour. The lubricant solution was filtered with use of a membrane filter. A residue was dried at a room temperature for 15 hours to obtain the graphite on which the lubricant adsorbed. Thermogravimetry was carried out with use of the graphite and a thermogravimetric analyzer (TG/DTA, available from EXTER). The graphite was heated to 550° C. at a rate of temperature rise of 2° C./min under a nitrogen atmosphere. The ratio of the mass of the lubricant which adsorbed on the graphite to the mass of the graphite was measured.

[Siloxane Resistance Evaluation]

The graphite (0.1 g) on which an arbitrary amount of the lubricant (described later) adsorbed was weighed and taken into a Petri dish. The Petri dish in which the graphite on which the lubricant adsorbed was placed and a vial in which octamethylcyclotetrasiloxane (0.5 g, hereinafter referred to as D4 in this specification) available from Tokyo Chemical Industry Co., Ltd. was placed were placed in a single container, and then the container was sealed. By leaving the container at a room temperature (25° C.) for 24 hours, the graphite on which the lubricant adsorbed was exposed to D4. Thereafter, the Petri dish was taken out from the container, and then D4 adhering to the graphite was extracted by adding methanol (2.2 g). After the methanol in which D4 was extracted was filtered with use of a membrane filter, a resulting filtrate was analyzed with use of a gas chromatograph (product number: HP6890, available from HEWLETT PACKARD) to measure the amount of D4 adhering to the graphite.

Note that the amount of the lubricant which adsorbed on the graphite was measured in the same manner as in the foregoing adsorbability evaluation.

Example 1

A compound 1 represented by the following formula was synthesized as below.

Note that the compound 1 corresponds to a compound represented by formula (1) wherein $R^1$ is a naphthyl group, $R^2$ is a Demnum skeleton, and $R^3$ is a hydrocarbon group having a dihydroxypropoxy group.

First, 12.0 g of 2-naphthol and 193.0 g of epichlorohydrin were introduced into a flask and heated to 70° C. To a resulting mixture, 10.3 g of potassium t-butoxide which was dissolved in 80.0 g of t-butyl alcohol was added dropwise, and then the resulting mixture was heated and stirred for 18 hours. A reaction product obtained after a reaction system was returned to a room temperature was washed with water, and then refined with use of MPLC to obtain 12.6 g of 2-[(2-naphthalenyloxy)methyl]-oxirane.

Into a flask, 7.8 g of this compound, 40.2 g of perfluoropolyether (number average molecular weight: 1194) represented by HO—CH$_2$CF$_2$CF$_2$O—(CF$_2$CF$_2$CF$_2$O)$_m$CF$_2$CF$_2$CH$_2$—OCH$_2$CH(OH)CH$_2$OH, 30.4 g of t-butyl alcohol, and 0.7 g of potassium t-butoxide were introduced, and stirred at 70° C. for 16 hours under an argon atmosphere. Thereafter, a resulting reaction product was neutralized, washed with water, and then further refined with use of a silica gel chromatograph to obtain 14.0 g of the compound 1. Results of identification of the compound 1 which was carried out by NMR are shown below.

$^{19}$F-NMR (solvent: none, reference: OCF$_2$CF$_2$CF$_2$O in the product was regarded as −129.7 ppm)

As a result of $^{19}$F-NMR, it was found that, in the compound 1, m=6.1.

$^1$H-NMR (solvent: none, reference substance: D$_2$O)

The resulting compound 1 was used as a lubricant in Example 1.

Example 2

A compound 2 represented by the following formula was synthesized as below.

Note that the compound 2 corresponds to a compound represented by formula (1) wherein $R^1$ is a phenoxyphenyl group, $R^2$ is a Demnum skeleton, and $R^3$ is a hydrocarbon group having a dihydroxypropoxy group.

First, 40.8 g of 4-phenoxyphenol and 412.5 g of epichlorohydrin were introduced into a flask and heated to 70° C. To a resulting mixture, 27.0 g of potassium t-butoxide which was dissolved in 200.5 g of t-butyl alcohol was added dropwise, and then the resulting mixture was heated and stirred for 18 hours. A reaction product obtained after a reaction system was returned to a room temperature was washed with water, and then refined with use of MPLC to obtain 30.2 g of 2-[(4-phenoxyphenoxy)methyl]-oxirane.

Into a flask, 9.4 g of this compound, 40.2 g of perfluoropolyether (number average molecular weight: 1194) represented by HO—CH$_2$CF$_2$CF$_2$O—(CF$_2$CF$_2$CF$_2$O)$_m$CF$_2$CF$_2$CH$_2$—OCH$_2$CH(OH)CH$_2$OH, 25.2 g of t-butyl alcohol, and 0.7 g of potassium t-butoxide were introduced, and stirred at 70° C. for 16 hours under an argon atmosphere. Thereafter, a resulting reaction product was neutralized, washed with water, and then further refined with use of a silica gel chromatograph to obtain 15.2 g of the compound 2. Results of identification of the compound 2 which was carried out by NMR are shown below.

$^{19}$F-NMR (solvent: none, reference: OCF$_2$CF$_2$CF$_2$O in the product was regarded as −129.7 ppm)

δ=−129.7 ppm, −129.6 ppm [12F, —OCF$_2$CF$_2$CF$_2$O—]

δ=−123.9 ppm [4F, —OCH$_2$CF$_2$CF$_2$O—]

δ=−86.3 ppm [4F, —OCH$_2$CF$_2$CF$_2$O—]

δ=−84.4 ppm [25F, —OCF$_2$CF$_2$CF$_2$O—]

As a result of $^{19}$F-NMR, it was found that, in the compound 2, m=6.3.

$^1$H-NMR (solvent: none, reference substance: D$_2$O)

δ=3.1 ppm to 4.5 ppm [17H, HO—CH$_2$CH(OH)CH$_2$O—CH$_2$CF$_2$CF$_2$O—, C$_6$H$_5$—O—C$_6$H$_4$—OCH$_2$CH(OH)CH$_2$O—CH$_2$CF$_2$CF$_2$O—]

δ=6.4 ppm to 7.4 ppm [9H, C$_6$H$_5$—O—C$_6$H$_4$—O—]

The resulting compound 2 was used as a lubricant in Example 2.

Example 3

A compound 3 represented by the following formula was synthesized as below.

C$_{10}$H$_7$O—CH$_2$CH(OH)CH$_2$O—CH$_2$CF$_2$CF$_2$O—(CF$_2$CF$_2$CF$_2$O)$_m$CF$_2$CF$_2$CF$_3$

Note that the compound 3 corresponds to a compound represented by formula (1) wherein R$^1$ is a naphthyl group, R$^2$ is a Demnum skeleton, and R$^3$ is a trifluoromethyl group.

In the same manner as in Example 1, 22.7 g of the compound 3 was obtained, except that HO—CH$_2$CF$_2$CF$_2$O—(CF$_2$CF$_2$CF$_2$O)$_m$CF$_2$CF$_2$CF$_3$ was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 3 which was carried out by NMR are shown below.

$^{19}$F-NMR (solvent: none, reference: OCF$_2$CF$_2$CF$_2$O in the product was regarded as −129.7 ppm)

δ=−130.7 ppm [2F, CF$_3$CF$_2$CF$_2$O—]

δ=−129.7 ppm, −129.6 ppm [11F, —OCF$_2$CF$_2$CF$_2$O—]

δ=−123.9 ppm [2F, —CH$_2$CF$_2$CF$_2$O—]

δ=−86.5 ppm [2F, —CH$_2$CF$_2$CF$_2$O—]

δ=−84.3 ppm to −83.6 ppm [22F, —OCF$_2$CF$_2$CF$_2$O—]

δ=−85.0 ppm [2F, CF$_3$CF$_2$CF$_2$O—]

δ=−82.9 ppm [3F, CF$_3$CF$_2$CF$_2$O—]

As a result of $^{19}$F-NMR, it was found that, in the compound 3, m=5.5.

$^1$H-NMR (solvent: none, reference substance: D$_2$O)

δ=3.0 ppm to 4.4 ppm [8H, C$_{10}$H$_7$O—CH$_2$CH(OH)CH$_2$O—CH$_2$CF$_2$CF$_2$O—]

δ=6.5 ppm to 7.6 ppm [7H, C$_{10}$H$_7$O—]

The resulting compound 3 was used as a lubricant in Example 3.

Example 4

A compound 4 represented by the following formula was synthesized as below.

C$_6$H$_5$—O—C$_6$H$_4$O—CH$_2$CH(OH)CH$_2$O—CH$_2$CF$_2$CF$_2$O—(CF$_2$CF$_2$CF$_2$O)$_m$CF$_2$CF$_2$CF$_3$

Note that the compound 4 corresponds to a compound represented by formula (1) wherein R$^1$ is a phenoxyphenyl group, R$^2$ is a Demnum skeleton, and R$^3$ is a trifluoromethyl group.

In the same manner as in Example 2, 24.2 g of the compound 4 was obtained, except that HO—CH$_2$CF$_2$CF$_2$O—(CF$_2$CF$_2$CF$_2$O)$_m$CF$_2$CF$_2$CF$_3$ was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 4 which was carried out by NMR are shown below.

$^{19}$F-NMR (solvent: none, reference: OCF$_2$CF$_2$CF$_2$O in the product was regarded as −129.7 ppm)

δ=−130.7 ppm [2F, CF$_3$CF$_2$CF$_2$O—]

δ=−129.7 ppm, −129.6 ppm [11F, —OCF$_2$CF$_2$CF$_2$O—]

δ=−123.9 ppm [2F, —CH$_2$CF$_2$CF$_2$O—]

δ=−86.5 ppm [2F, —CH$_2$CF$_2$CF$_2$O—]

δ=−84.3 ppm to −83.6 ppm [22F, —OCF$_2$CF$_2$CF$_2$O—]

δ=−85.0 ppm [2F, CF$_3$CF$_2$CF$_2$O—]

δ=−82.9 ppm [3F, CF$_3$CF$_2$CF$_2$O—]

As a result of $^{19}$F-NMR, it was found that, in the compound 4, m=5.5.

$^1$H-NMR (solvent: none, reference substance: D$_2$O)

δ=3.0 ppm to 4.4 ppm [8H, C$_6$H$_5$—O—C$_6$H$_4$O—CH$_2$CH(OH)CH$_2$O—CH$_2$CF$_2$CF$_2$O—]

δ=6.4 ppm to 7.3 ppm [9H, C$_6$H$_5$—O—C$_6$H$_4$O—]

The resulting compound 4 was used as a lubricant in Example 4.

Example 5

A compound 5 represented by the following formula was synthesized as below.

C$_6$H$_5$—O—C$_6$H$_4$—OCH$_2$CH(OH)CH$_2$O—CH$_2$CF$_2$O—(CF$_2$CF$_2$O)$_l$CF$_2$CH$_2$O—CH$_2$CH(OH)CH$_2$OH

Note that the compound 5 corresponds to a compound represented by formula (1) wherein R$^1$ is a phenoxyphenyl group, R$^2$ is a C$_2$ skeleton, and R$^3$ is a hydrocarbon group having a dihydroxypropoxy group.

In the same manner as in Example 2, 13.3 g of the compound 5 was obtained, except that HO—CH$_2$CF$_2$O—(CF$_2$CF$_2$O)$_l$CF$_2$CH$_2$—OCH$_2$CH(OH)CH$_2$OH (number average molecular weight: 1092) was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 5 which was carried out by NMR are shown below.

$^{19}$F-NMR (solvent: none, reference: OCF$_2$CF$_2$O in the product was regarded as −90.7 ppm)

$\delta$=−90.7 ppm [28F, —CF$_2$CF$_2$O—]

$\delta$=−79.8 ppm [4F, —CH$_2$CF$_2$O—]

As a result of $^{19}$F-NMR, it was found that, in the compound 5, l=7.0.

$^1$H-NMR (solvent: none, reference substance: D$_2$O)

$\delta$=3.1 ppm to 4.5 ppm [17H, HO—CH$_2$CH(OH)CH$_2$O—CH$_2$CF$_2$O—, C$_6$H$_5$—O—C$_6$H$_4$—OCH$_2$CH(OH)CH$_2$O—CH$_2$CF$_2$O—]

$\delta$=6.4 ppm to 7.3 ppm [9H, C$_6$H$_5$—O—C$_6$H$_4$—O—]

The resulting compound 5 was used as a lubricant in Example 5.

Example 6

A compound 6 represented by the following formula was synthesized as below.

C$_6$H$_5$—O—C$_6$H$_4$—OCH$_2$CH(OH)CH$_2$O—CH$_2$CF$_2$O—(CF$_2$O)$_z$(CF$_2$CF$_2$O)$_l$CF$_2$CH$_2$O—CH$_2$CH(OH)CH$_2$OH

Note that the compound 6 corresponds to a compound represented by formula (1) wherein R$^1$ is a phenoxyphenyl group, R$^2$ is a Fomblin skeleton, and R$^3$ is a hydrocarbon group having a dihydroxypropoxy group.

In the same manner as in Example 2, 16.2 g of the compound 6 was obtained, except that HO—CH$_2$CF$_2$O—(CF$_2$O)$_z$(CF$_2$CF$_2$O)$_l$CF$_2$CH$_2$—OCH$_2$CH(OH)CH$_2$OH (number average molecular weight: 1378) was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 6 which was carried out by NMR are shown below.

$^{19}$F-NMR (solvent: none, reference: OCF$_2$OCF$_2$CF$_2$OCF$_2$— in the product was regarded as −90.7 ppm)

$\delta$=−52.1 ppm, −53.7 ppm, −55.4 ppm [12F, —OCF$_2$O—]

$\delta$=−89.1 ppm, −90.7 ppm [24F, —OCF$_2$CF$_2$O—]

$\delta$=−77.9 ppm, −80.0 ppm [4F, —OCF$_2$CH$_2$O—]

As a result of $^{19}$F-NMR, it was found that, in the compound 6, l=6.1 and z=6.4.

$^1$H-NMR (solvent: none, reference substance: D$_2$O)

$\delta$=3.2 ppm to 4.4 ppm [17H, HO—CH$_2$CH(OH)CH$_2$O—CH$_2$CF$_2$O—, C$_6$H$_5$—O—C$_6$H$_4$—OCH$_2$CH(OH)CH$_2$O—CH$_2$CF$_2$O—]

$\delta$=6.4 ppm to 7.4 ppm [9H, C$_6$H$_5$—O—C$_6$H$_4$—O—]

The resulting compound 6 was used as a lubricant in Example 6.

Example 7

A compound 7 represented by the following formula was synthesized as below.

C$_{10}$H$_7$—OCH$_2$CH(OH)CH$_2$O—CH$_2$CF$_2$CF$_2$O—(CF$_2$CF$_2$CF$_2$O)$_m$CF$_2$CF$_2$CH$_2$O—CH$_2$CH(OH)CH$_2$O—C$_{10}$H$_7$

Note that the compound 7 corresponds to a compound represented by formula (1) wherein R$^1$ is a naphthyl group, R$^2$ is a Demnum skeleton, and R$^3$ is a hydrocarbon group having a naphthyl group.

In the same manner as in Example 1, 20.2 g of the compound 7 was obtained, except that HO—CH$_2$CF$_2$CF$_2$O—(CF$_2$CF$_2$CF$_2$O)$_m$CF$_2$CF$_2$CH$_2$OH (number average molecular weight: 1122) was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 7 which was carried out by NMR are shown below.

$^{19}$F-NMR (solvent: none, reference: OCF$_2$CF$_2$CF$_2$O in the product was regarded as −129.7 ppm)

$\delta$=−129.7 ppm, −129.6 ppm [12F, —OCF$_2$CF$_2$CF$_2$O—]

$\delta$=−123.9 ppm [4F, —OCH$_2$CF$_2$CF$_2$O—]

$\delta$=−86.3 ppm [4F, —OCH$_2$CF$_2$CF$_2$O—]

$\delta$=−84.4 ppm [25F, —OCF$_2$CF$_2$CF$_2$O—]

As a result of $^{19}$F-NMR, it was found that, in the compound 7, m=6.3.

$^1$H-NMR (solvent: none, reference substance: D$_2$O)

$\delta$=3.1 ppm to 4.5 ppm [16H, C$_{10}$H$_7$—OCH$_2$CH(OH)CH$_2$O—CH$_2$CF$_2$CF$_2$O—]

$\delta$=6.5 ppm to 7.6 ppm [14H, C$_{10}$H$_7$—]

The resulting compound 7 was used as a lubricant in Example 7.

Example 8

A compound 8 represented by the following formula was synthesized as below.

C$_6$H$_5$O—C$_6$H$_4$—OCH$_2$CH(OH)CH$_2$O—CH$_2$CF$_2$CF$_2$O—(CF$_2$CF$_2$CF$_2$O)$_m$CF$_2$CF$_2$CH$_2$O—CH$_2$CH(OH)CH$_2$O—C$_6$H$_4$—OC$_6$H$_5$

Note that the compound 8 corresponds to a compound represented by formula (1) wherein R$^1$ is a phenoxyphenyl group, R$^2$ is a Demnum skeleton, and R$^3$ is a hydrocarbon group having a phenoxyphenyl group.

In the same manner as in Example 2, 22.8 g of the compound 8 was obtained, except that HO—CH$_2$CF$_2$CF$_2$O—(CF$_2$CF$_2$CF$_2$O)$_m$CF$_2$CF$_2$CH$_2$OH (number average molecular weight: 1122) was used instead of HO—CH$_2$CF$_2$CF$_2$O—(CF$_2$CF$_2$CF$_2$O)$_m$CF$_2$CF$_2$CH$_2$—OCH$_2$CH(OH)CH$_2$OH. Results of identification of the compound 8 which was carried out by NMR are shown below.

$^{19}$F-NMR (solvent: none, reference: OCF$_2$CF$_2$CF$_2$O in the product was regarded as −129.7 ppm)

$\delta$=−129.7 ppm, −129.6 ppm [12F, —OCF$_2$CF$_2$CF$_2$O—]

$\delta$=−123.9 ppm [4F, —OCH$_2$CF$_2$CF$_2$O—]

$\delta$=−86.3 ppm [4F, —OCH$_2$CF$_2$CF$_2$O—]

$\delta$=−84.4 ppm [25F, —OCF$_2$CF$_2$CF$_2$O—]

As a result of $^{19}$F-NMR, it was found that, in the compound 8, m=6.3.

$^1$H-NMR (solvent: none, reference substance: D$_2$O)

$\delta$=3.1 ppm to 4.5 ppm [16H, C$_6$H$_5$—O—C$_6$H$_4$—OCH$_2$CH(OH)CH$_2$O—CH$_2$CF$_2$CF$_2$O—]

$\delta$=6.4 ppm to 7.4 ppm [18H, C$_6$H$_5$—O—C$_6$H$_4$—O—]

The resulting compound 8 was used as a lubricant in Example 8.

Example 9

A compound 9 represented by the following formula was synthesized as below.

$$C_{10}H_7O-CH_2CH(OH)CH_2O-CH_2CF_2CF_2CF_2O-(CF_2CF_2CF_2O)_nCF_2CF_2CF_2CH_2O-CH_2CH(OH)CH_2-OC_{10}H_7$$

Note that the compound 9 corresponds to a compound represented by formula (1) wherein $R^1$ is a naphthyl group, $R^2$ is a $C_4$ skeleton, and $R^3$ is a hydrocarbon group having a naphthyl group.

In the same manner as in Example 1, 20.5 g of the compound 9 was obtained, except that $HO-CH_2CF_2CF_2CF_2O-(CF_2CF_2CF_2O)_nCF_2CF_2CF_2CH_2OH$ (number average molecular weight: 1183) was used instead of $HO-CH_2CF_2CF_2O-(CF_2CF_2CF_2O)_mCF_2CF_2CH_2-OCH_2CH(OH)CH_2OH$. Results of identification of the compound 9 which was carried out by NMR are shown below.

$^{19}$F-NMR (solvent: none, reference: $OCF_2CF_2CF_2O$ in the product was regarded as −126.2 ppm)

δ=−127.3 ppm [4F, —$OCF_2CF_2CF_2CH_2O$—]

δ=−126.2 ppm [15F, —$OCF_2CF_2CF_2O$—]

δ=−120.5 ppm [4F, —$OCF_2CF_2CF_2CH_2O$—]

δ=−83.8 ppm [4F, —$OCF_2CF_2CF_2CF_2O$—, —$OCF_2CF_2CF_2CH_2O$—]

As a result of $^{19}$F-NMR, it was found that, in the compound 9, n=3.7.

$^1$H-NMR (solvent: none, reference substance: $D_2O$)

δ=3.1 ppm to 4.5 ppm [16H, $C_{10}H_7O-CH_2CH(OH)$ $CH_2O-CH_2CF_2CF_2O-$]

δ=6.4 ppm to 7.6 ppm [14H, $C_{10}H_7O-$]

The resulting compound 9 was used as a lubricant in Example 9.

Example 10

A compound 10 represented by the following formula was synthesized as below.

$$C_{10}H_7O-CH_2CH(OH)CH_2O-CH_2CF_2CF_2O-(CF_2CF_2CF_2O)_mCF_2CF_2CH_2O-CH_2CH(OH)CH_2-OC_6H_4-OC_6H_5$$

Note that the compound 10 corresponds to a compound represented by formula (1) wherein $R^1$ is a naphthyl group, $R^2$ is a Demnum skeleton, and $R^3$ is a hydrocarbon group having a phenoxyphenyl group.

Into a flask, 17.5 g of 2-[(2-naphthalenyloxy)methyl]-oxirane synthesized in Example 1, 98.0 g of perfluoropolyether (number average molecular weight: 1122) represented by $HO-CH_2CF_2CF_2O-(CF_2CF_2CF_2O)_mCF_2CF_2CH_2-OH$, 220 g of t-butyl alcohol, and 2.0 g of potassium t-butoxide were introduced, and stirred at 70° C. for 16 hours under an argon atmosphere. Thereafter, a resulting reaction product was neutralized, washed with water, and then further refined with use of a silica gel chromatograph to obtain 43.1 g of perfluoropolyether having a naphthyl group at only one terminal thereof. Into a flask, 40 g of this perfluoropolyether, 5.5 g of 2-[(4-phenoxyphenoxy)methyl]-oxirane, 293 g of t-butyl alcohol, and 0.3 g of potassium t-butoxide were introduced, and stirred at 70° C. for 16 hours under an argon atmosphere. Thereafter, a resulting reaction product was neutralized, washed with water, and then further refined with use of a silica gel chromatograph to obtain 32.5 g of the compound 10. Results of identification of the compound 10 which was carried out by NMR are shown below.

$^{19}$F-NMR (solvent: none, reference: $OCF_2CF_2CF_2O$ in the product was regarded as −129.7 ppm)

δ=−129.7 ppm, −129.6 ppm [12F, —$OCF_2CF_2CF_2O$—]

δ=−123.9 ppm [4F, —$OCH_2CF_2CF_2O$—]

δ=−86.3 ppm [4F, —$OCH_2CF_2CF_2O$—]

δ=−84.4 ppm [24F, —$OCF_2CF_2CF_2O$—]

As a result of $^{19}$F-NMR, it was found that, in the compound 10, m=6.1.

$^1$H-NMR (solvent: none, reference substance: $D_2O$)

δ=3.1 ppm to 4.5 ppm [16H, $C_{10}H_7-OCH_2CH(OH)$ $CH_2O-CH_2CF_2CF_2O-$, $C_6H_5O-C_6H_4O-$ $CH_2CH(OH)CH_2O-CH_2CF_2CF_2O-$]

δ=6.4 ppm to 7.6 ppm [7H, $C_{10}H_7-$, $C_6H_5O-$ $C_6H_4O-$]

The resulting compound 10 was used as a lubricant in Example 10.

Comparative Example 1

As a lubricant in Comparative Example 1, a compound 11 having a Demnum skeleton, having a methoxyphenyl group at one terminal thereof, and having a dihydroxypropoxy group at the other terminal thereof as below was used.

$$MeO-C_6H_4-OCH_2CH(OH)CH_2O-CH_2CF_2CF_2O-(CF_2CF_2CF_2O)_mCF_2CF_2CH_2OCH_2CH(OH)CH_2OH$$

Note, here, that m=7.2.

Comparative Example 2

As a lubricant in Comparative Example 2, a compound 12 having a Demnum skeleton and having methoxyphenyl groups at both terminals thereof as below was used.

$$MeO-C_6H_4-OCH_2CH(OH)CH_2O-CH_2CF_2CF_2O-(CF_2CF_2CF_2O)_mCF_2CF_2CH_2 CH_2CH(OH) CH_2O-C_6H_4-OMe$$

Note, here, that m=7.5.

Comparative Example 3

As a lubricant in Comparative Example 3, a compound 13 having a Demnum skeleton and having dihydroxypropoxy groups at both terminals thereof as below was used.

$$HOCH_2CH(OH)CH_2O-CH_2CF_2CF_2O-(CF_2CF_2CF_2O)_mCF_2CF_2CH_2O\ CH_2CH(OH)CH_2OH$$

Note, here, that m=6.1.

[Results of Adsorbability Evaluation and Siloxane Resistance Evaluation]

Shown in Table 1 are results of measurement of the amounts of lubricants which adsorbed on graphite in a case where the concentrations of the lubricants in Vertrel-XF (150 g) (registered trademark) (available from DuPont) solutions were 0.1 wt %.

TABLE 1

| | Lubricant | Amount of lubricant which adsorbed on graphite (wt %) |
|---|---|---|
| Example 1 | Compound 1 | 2.27 |
| Example 2 | Compound 2 | 2.30 |
| Example 3 | Compound 3 | 2.14 |
| Example 4 | Compound 4 | 2.16 |
| Example 5 | Compound 5 | 2.36 |
| Example 6 | Compound 6 | 2.22 |
| Example 7 | Compound 7 | 2.42 |
| Example 8 | Compound 8 | 2.55 |
| Example 9 | Compound 9 | 2.54 |
| Example 10 | Compound 10 | 2.47 |
| Comparative Example 1 | Compound 11 | 1.82 |
| Comparative Example 2 | Compound 12 | 1.51 |
| Comparative Example 3 | Compound 13 | 1.20 |

From Table 1, it was found that larger amounts of the lubricants adsorbed on the graphite in Examples 1 to 10 than in Comparative Examples 1 to 3. In other words, it was found that a compound in accordance with an embodiment of the present invention has excellent affinity for a carbon material.

Next, shown in Table 2 are the amounts of D4 which adhered to the graphite and the amounts of the lubricants which adsorbed on the graphite.

TABLE 2

| | Lubricant | Amount of lubricant which adsorbed on graphite (wt %) | Amount of D4 which adhered to graphite (ppm) |
|---|---|---|---|
| Example 1 | Compound 1 | 1.38 | 2503 |
| Example 2 | Compound 2 | 1.38 | 2331 |
| Example 3 | Compound 3 | 1.41 | 4772 |
| Example 4 | Compound 4 | 1.39 | 4699 |
| Example 5 | Compound 5 | 1.45 | 2375 |
| Example 6 | Compound 6 | 1.39 | 2436 |
| Example 7 | Compound 7 | 1.35 | 2578 |
| Example 8 | Compound 8 | 1.37 | 2456 |
| Example 9 | Compound 9 | 1.41 | 2534 |
| Example 10 | Compound 10 | 1.42 | 2523 |
| Comparative Example 1 | Compound 11 | 1.40 | 5664 |
| Comparative Example 2 | Compound 12 | 1.45 | 5388 |
| Comparative Example 3 | Compound 13 | 1.42 | 6122 |

From Table 2, it was found that smaller amounts of the D4 adhered to the graphite in Examples 1 to 10 than in Comparative Examples 1 to 3. In other words, it was found that impurities such as siloxane are less likely to adhere to a carbon protective film in Examples 1 to 10. Therefore, it was found that a lubricant in accordance with an embodiment of the present invention, which has a naphthyl group or a phenoxyphenyl group, has more excellent siloxane resistance than a conventional lubricant.

INDUSTRIAL APPLICABILITY

A perfluoropolyether compound in accordance with an aspect of the present invention can be suitably used as a lubricant for magnetic disks.

REFERENCE SIGNS LIST

1 Magnetic disk
2 Lubricant layer
3 Protective film layer (protective layer)
4 Recording layer
5 Lower layer
6 Soft magnetic lower layer
7 Adhesive layer
8 Non-magnetic substrate

The invention claimed is:

1. A flourine-containing ether compound represented by the following formula (1):

$$R^1-OCH_2CH(OH)CH_2OCH_2-R^2-R^3 \quad (1)$$

wherein: $R^1$ is a naphthyl group represented by $C_{10}H_7-$ or a phenoxyphenyl group represented by $C_6H_5-OC_6H_4-$;

$R^2$ is  $-(CF_2)_x(CF(CF_3))_yO(CF_2O)_z(CF_2CF_2O)_l(CF_2CF_2CF_2O)_m(CF_2CF_2CF_2CF_2O)_n(CF(CF_3)CF_2O)_o(CF(CF_3))_y(CF_2)_x-$, wherein x is a real number of 0 to 3, y is a real number of 0 to 1, z, l, m, n, and o are each independently a real number of 0 to 15, and any one of x and y is a real number of 1 or more and at least any one of z, l, m, n, and o is a real number of 1 or more; and $R^3$ is a hydrocarbon group having a naphthyl group represented by $-CH_2OCH_2CH(OH)CH_2O-C_{10}H_7$, a hydrocarbon group having a phenoxyphenyl group represented by $-CH_2OCH_2CH(OH)CH_2O-C_6H_4-OC_6H_5$, a hydrocarbon group having a methoxyphenyl group represented by $-CH_2OCH_2CH(OH)CH_2O-C_6H_4-OMe$, or $-CH_2O(CH_2CH(OH)CH_2O)_tH$ or $-(CF_2)_uCF_3$, wherein t is a real number of 0 to 5 and u is a real number of 0 to 3.

2. A lubricant comprising the fluorine-containing ether compound recited in claim 1.

3. A magnetic disk comprising:
a recording layer;
a protective layer disposed on the recording layer; and
a lubricant layer disposed on the protective layer,
the lubricant layer containing the lubricant recited in claim 2.

* * * * *